(12) United States Patent
Locke et al.

(10) Patent No.: US 8,725,528 B2
(45) Date of Patent: May 13, 2014

(54) SYSTEM AND METHOD FOR MANAGING HISTORY OF PATIENT AND WOUND THERAPY TREATMENT

(75) Inventors: Christopher Brian Locke, Bournemouth (GB); Mark Stephen James Beard, Ferndown (GB); Thomas Paul Lawhorn, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 522 days.

(21) Appl. No.: 11/901,601

(22) Filed: Sep. 18, 2007

(65) Prior Publication Data

US 2008/0228526 A1 Sep. 18, 2008

Related U.S. Application Data

(60) Provisional application No. 60/845,993, filed on Sep. 19, 2006.

(51) Int. Cl.
*G06Q 10/00* (2012.01)
*G06Q 50/00* (2012.01)
*A61M 31/00* (2006.01)

(52) U.S. Cl.
USPC .................................. 705/2; 705/3; 604/313

(58) Field of Classification Search
USPC .......................................... 705/2–3; 604/313
See application file for complete search history.

(56) References Cited

U.S. PATENT DOCUMENTS

| | | | |
|---|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |

(Continued)

FOREIGN PATENT DOCUMENTS

| AU | 550575 A1 | 8/1982 |
|---|---|---|
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksa , U.S.S.R. 1986);pp. 94-96 (certified translation).

(Continued)

*Primary Examiner* — Minnah Seoh

(57) ABSTRACT

A tissue treatment system including a processing unit executing software, an electronic display in communication with the processing unit, and a storage unit in communication with the processing unit. The software may be configured to cause the processing unit to manage a patient history database, treatment history database, and image history database. The processing unit may further be configured to enable a clinician to access and display information stored in any of the databases.

20 Claims, 7 Drawing Sheets

(56) References Cited

U.S. PATENT DOCUMENTS

| | | |
|---|---|---|
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,911,687 A | 6/1999 | Sato et al. |
| 6,032,678 A * | 3/2000 | Rottem .................... 600/437 |
| 6,047,259 A * | 4/2000 | Campbell et al. ................ 705/3 |
| 6,071,267 A | 6/2000 | Zamierowski |
| 6,091,981 A | 7/2000 | Cundari et al. |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0019751 A1* | 2/2002 | Rothschild et al. ............... 705/3 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0008523 A1* | 1/2004 | Butler .......................... 362/551 |
| 2004/0078236 A1 | 4/2004 | Stoodley et al. |
| 2004/0122705 A1 | 6/2004 | Sabol et al. |
| 2005/0102009 A1 | 5/2005 | Costantino |
| 2005/0261642 A1 | 11/2005 | Weston |
| 2006/0072804 A1 | 4/2006 | Watson et al. |
| 2006/0074722 A1 | 4/2006 | Chu |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0836831 A2 | 4/1998 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| JP | 2006-149654 | 6/2006 |
| SG | 71559 | 4/2002 |
| TW | 200612268 A | 4/2006 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | 99/49775 A2 | 10/1999 |
| WO | 2005060466 A2 | 7/2005 |

OTHER PUBLICATIONS

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin*

(56) References Cited

OTHER PUBLICATIONS (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Extended European Search Report for corresponding EP07838545. 7, mailed Aug. 2, 2013.

Examination Report date mailed Sep. 15, 2010 for New Zealand Application No. 575128.

\* cited by examiner

SYSTEM AND METHOD FOR MANAGING HISTORY OF PATIENT AND WOUND THERAPY TREATMENT

CROSS-REFERENCE TO RELATED APPLICATIONS

This application claims the benefit of U.S. Provisional Patent Application No. 60/845,993 filed on Sep. 19, 2006, which is hereby incorporated by reference.

BACKGROUND OF THE INVENTION

1. Field of the Invention

The principles of the present invention generally relate to managing information associated with patient and treatment history, and, more specifically but not by way of limitation, to a system and method for enabling a clinician using a tissue treatment system to store patient history, treatment history, and photographs of wounds on the tissue treatment system for use in determining continued tissue treatment using the tissue treatment system.

2. Description of the Related Art

The field of wound therapy has advanced in recent years. One of the advancements of wound healing therapy has been the development of vacuum assisted wound healing. The application of reduced or negative pressure to a wound has been clinically shown to improve blood flow at the wound or tissue site, increase tissue growth, reduce infection, and improve healing time. Caregivers and clinicians may use such vacuum assisted wound healing to treat a variety of chronic and acute wound types, such as pressure ulcers, diabetic wounds, abdominal wounds, partial-thickness burns, trauma wounds, flaps and grafts.

Background on Wounds and Wound Healing Processes

A wound is generally defined as a break in the epithelial integrity of the skin. Such an injury, however, may be much deeper, including the dermis, subcutaneous fat, fascia, muscle, and even bone. Proper wound healing is a highly complex, dynamic, and coordinated series of steps leading to tissue repair. Acute wound healing is a dynamic process involving both resident and migratory cell populations acting in a coordinated manner within the extra-cellular matrix environment to repair the injured tissues. Some wounds fail to heal in this manner (for a variety of reasons) and may be referred to as chronic wounds.

Following tissue injury, the coordinated healing of a wound will typically involve four overlapping but well-defined phases: hemostasis, inflammation, proliferation, and remodeling. Hemostasis involves the first steps in wound response and repair that are bleeding, coagulation, and platelet and complement activation. Inflammation peaks near the end of the first day. Cell proliferation occurs over the next 7-30 days and involves the time period over which wound area measurements may be of most benefit. During this time fibroplasia, angiogenesis, re-epithelialization, and extra-cellular matrix synthesis occur. The initial collagen formation in a wound typically peaks in approximately 7 days. The wound re-epithelialization occurs in about 48 hours under optimal conditions, at which time the wound may be completely sealed. A healing wound may have 15% to 20% of full tensile strength at 3 weeks and 60% of full strength at 4 months. After the first month, a degradation and remodeling stage begins, wherein cellularity and vascularity decrease and tensile strength increases. Formation of a mature scar often requires 6 to 12 months.

Efforts in the Related Art to Measure Wound Healing Processes

Commensurate with providing an effective wound therapy regimen is the ability to make measurements of the size of the wound and the rate at which it heals. Once course but generally effective manner of determining the rate of healing for a wound is to track changes in the overall wound size over time.

One way that clinicians have historically tracked wound healing is to take photographs of a wound over time and maintain the photographs in a patient's file so as to be able to review the photographs for changes of the wound over time. The clinician also establishes treatment programs for patients to treat wounds. As understood in the art, a patient may be treated in a medical facility or as an outpatient. Whether the patient is treated in a medical facility or at home, a common problem for clinicians is whether the treatment is properly executed. In the case of a patient being treated in a medical facility, there is potential for treatment settings to be incorrect, power to go out during treatment, vacuum pressure to be reduced due to a drape leak, canister becoming full and interrupting vacuum therapy, or any number of other reasons to cause tissue treatment not to be provided as prescribed by the clinician. In the case of the patient being treated at home using a tissue therapy system, the same issues exist as within the medical facility plus potential for the patient not to be diligent in following the clinician's treatment prescription. For example, the patients may conduct treatment sessions for too short or too long time periods, skip treatment sessions, or otherwise not follow the clinician's prescribed wound therapy treatments.

When a tissue treatment is not properly followed, the tissue does not heal properly and the clinician loses the ability to adequately diagnose and treat a wound or other tissue site. Because wound treatment can be costly in both materials and professional care time, a treatment that is based on a patient to accurately follow a treatment plan. Furthermore, an accurate assessment of the wound and the wound healing process can be essential.

SUMMARY OF THE INVENTION

To enable a clinician to accurately manage and monitor tissue treatment, the principles of the present invention provide for a tissue treatment system to utilize databases to store patient history and treatment history so that a clinician can verify that the patient is following the prescribed treatment and view historical information of a patient's tissue response to the treatment. In addition, the tissue treatment system may access a database including images and statistical information, such as tissue area, of a tissue site being treated. The clinician may use the information in the databases to make additional treatment decisions.

One embodiment of a system includes a tissue treatment system including a processing unit executing software, an electronic display in communication with the processing unit, and a storage unit in communication with the processing unit. The software may be configured to cause the processing unit to manage a patient history database, treatment history database, and image history database. The processing unit may further be configured to enable a clinician to access and display information stored in any of the databases.

One embodiment of a process for managing tissue treatment information may include storing patient history information, storing treatment history information, storing image history information of a tissue site of a patient, and accessing at least one record of patient, treatment, and image history information, where the image history information is indicative of results of tissue treatment to the tissue site. The record(s) may be displayed to enable a clinician to make tissue treatment decisions based on historical treatment provided to the patient and results of the tissue treatment to the tissue site being treated.

DETAILED DESCRIPTION OF THE DRAWINGS

Figure 1:
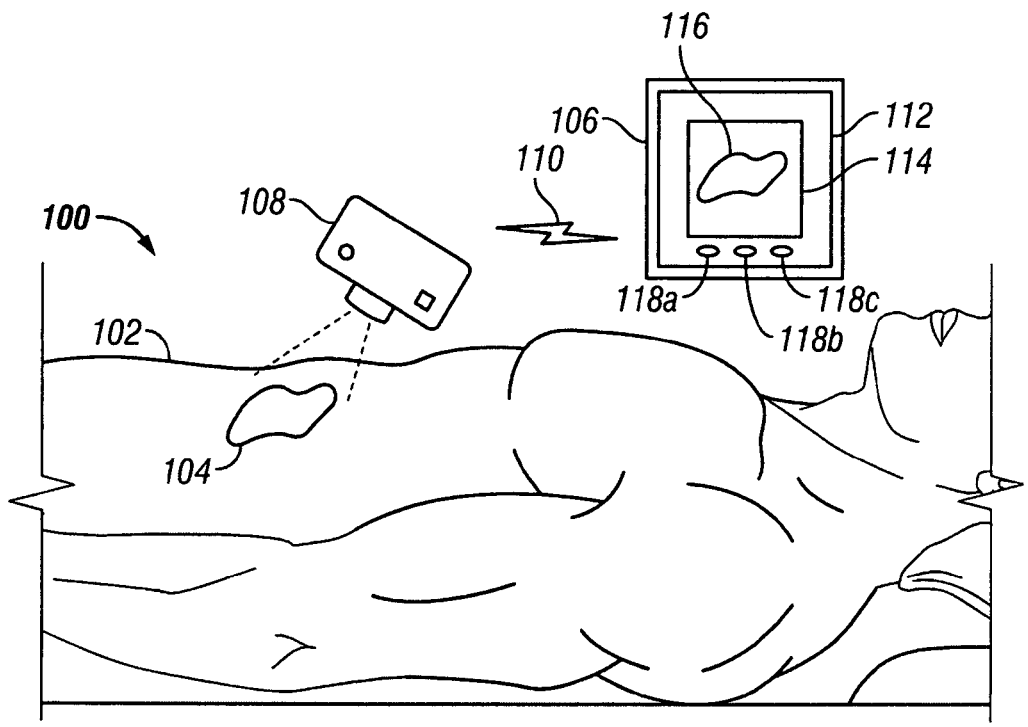
FIG. 1 is an illustration of an exemplary patient environment using a tissue treatment system in accordance with the principles of the present invention.

Referring to FIG. 1, an exemplary patient environment showing a patient 102 having a tissue site 104 using a tissue treatment system 106 in accordance with the principles of the present invention. In one embodiment, the tissue treatment system 106 may be a vacuum assisted therapy device. Alternatively, the tissue treatment system 106 may be any system that is generally utilized to assist a patient in the process of tissue treatment. Still yet, the tissue treatment system 106 may be any computing system that is configured to utilize software as described further herein to assist a caregiver or clinician with monitoring healing of the tissue site 104.

An image capture device 108 may be utilized to capture an image of the tissue site 104 in a photograph. The image capture device 108 may be a digital camera, mobile telephone, or any other electronic device configured to capture an image in a digital or analog format. In general, to expedite capturing and working with an image of the tissue site 104, a digital camera may be configured to establish a wireless communications link 110 with the tissue treatment system 106. The wireless communications link 110 may be an 802.11 wireless communications link or WiFi communications link. Any other wireless communications link protocol may be utilized. Alternatively or additionally, a wired connection may be made between the tissue treatment system 106 and the image capture device 108. Still yet, the image capture device 108 may utilize a memory device (not shown) that may be transferred between electronic devices. The memory device may include flash memory, memory stick, mini-DVD, or any other memory device that the tissue treatment system 106 may be compatible.

The term "tissue site" as used herein refers to a wound or defect located on or within any tissue, including but not limited to, bone tissue, adipose tissue, muscle tissue, neuro tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The term "clinician" is used herein as meaning any medical professional, user, family member of a patient, or patient who interacts or interfaces with a reduced pressure delivery system.

The tissue treatment system 106 may be configured to apply reduced pressure therapy by applying reduced pressure through a reduced pressure conduit (not shown) to a manifold (not shown) that is applied to the tissue site 104 being treated. In order for the clinician to properly monitor how well the tissue site 104 is healing, the image capture device 108 may capture images of the tissue site 104 over time. The images may be communicated to the tissue treatment system 106 and displayed on an electronic display 112. The tissue treatment system 106 may be configured to display a graphical user interface (GUI) 114 and have the image 116 of the tissue site 104 displayed thereon. The tissue treatment system 106 may store each of the images in an image database.

Soft-buttons 118a-118c or other graphical control elements may be disposed on the electronic display 112 to enable the clinician to enter a mode, edit an image, or perform any other control as definable by a developer and executed by the tissue treatment system 106. For example, a soft-button 118a may enable a user to draw traces around the image 116 of the tissue site 104 by using a stylus, computer mouse, finger, or any other method to trace around or select points on a perimeter of the image 116 of the tissue site 104. In response to completing a trace around the tissue site 104, the function initiated by pressing soft-button 118a may compute area within the trace. Another soft-button 118b may cause the tissue treatment system 106 to enter an image history mode, whereby historical images of the tissue site are presented and selectable by the clinician (see FIG. 13). Another soft-button 118c may cause a treatment history to be displayed for the current patient and current tissue site (see FIG. 12). It should be understood that any function to enable the clinician to collect, manipulate, edit, trace, define tissue types, etc., may be provided on the tissue treatment system 106.

Figure 2:
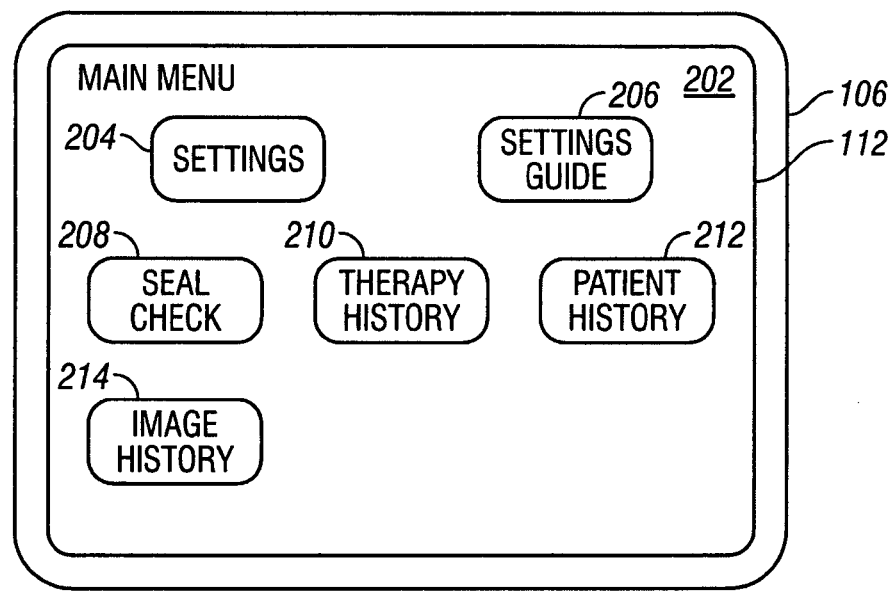
FIG. 2 is an illustration of an exemplary main menu graphical user interface to enable a clinician to control the tissue treatment system of FIG. 1.

Referring to FIG. 2, an exemplary graphical user interface 202 may be displayed on a touch-screen 112 of the tissue treatment system 106 and enable a clinician to select from a number of different options for controlling the tissue treatment system 106. One control option may include a "settings" soft-button 204 that enables a clinician to create a treatment setting. A "settings guide" soft-button 206 may provide information to instruct the clinician about different setting options and functions. A "seal check" soft-button 208 may enable the clinician to locate a seal leak at a drape covering a manifold that is being used in providing reduced pressure to a tissue site. A "therapy history" soft-button 210 may enable the clinician to display therapy or treatment history (FIG. 12). A "patient history" soft-button 212 may enable the clinician to display patient history (FIG. 11) recorded by the tissue treatment system 106. An "image history" soft-button 214 may enable the clinician to display images (FIG. 13) of one or more tissue sites taken over time. It should be understood that other functions to assist a clinician in treating a tissue site may be available in accordance with the principles of the present invention.

Figure 3:
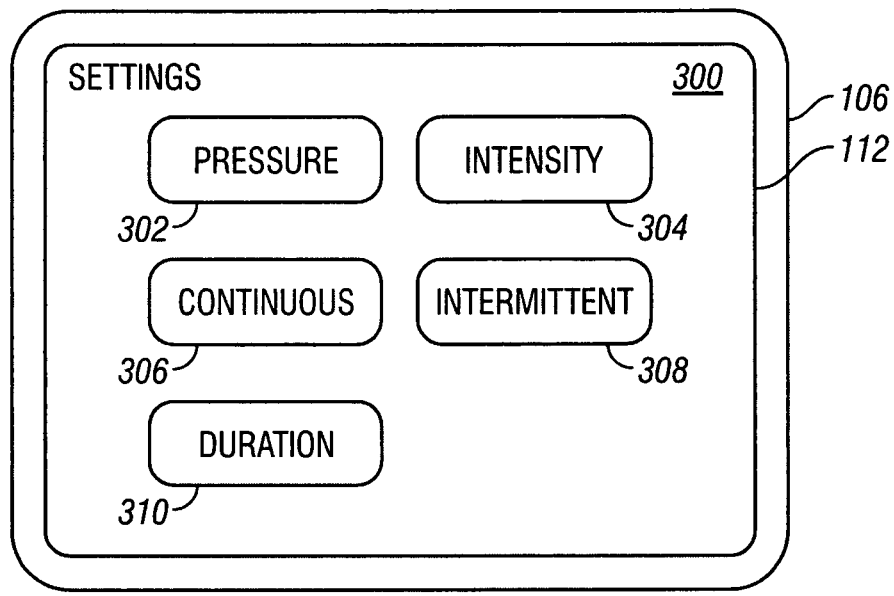
FIG. 3 is an illustration of an exemplary settings graphical user interface to enable a clinician to set up a tissue treatment for treating a tissue site of a patient.

Referring to FIG. 3, a Settings GUI 300 may be displayed in response to the clinician selecting the "settings" soft-button 204 (FIG. 2) on the touch-screen 112 of the tissue treatment system 106. As shown, a number of different soft-buttons are available for selection to select setting one or more tissue treatment parameters. The available selections include (i) "pressure" soft-button 302, (ii) "intensity" soft-button 304, (iii) "continuous" soft-button 306, (iv) "intermittent" soft-button 308, and (v) "duration" soft-button 310. Each of these soft-buttons may cause a separate screen to be displayed with one or more parameters available for selection or setting as associated with the selected function. Alternatively, rather than having separate screens for each function, the parameters of each function may be displayed and selectably altered by the clinician on the Settings GUI 300. It should be understood that nearly any GUI element or function may be utilized to enable the clinician to set-up a treatment for treating a tissue site of a patient.

Figure 4:
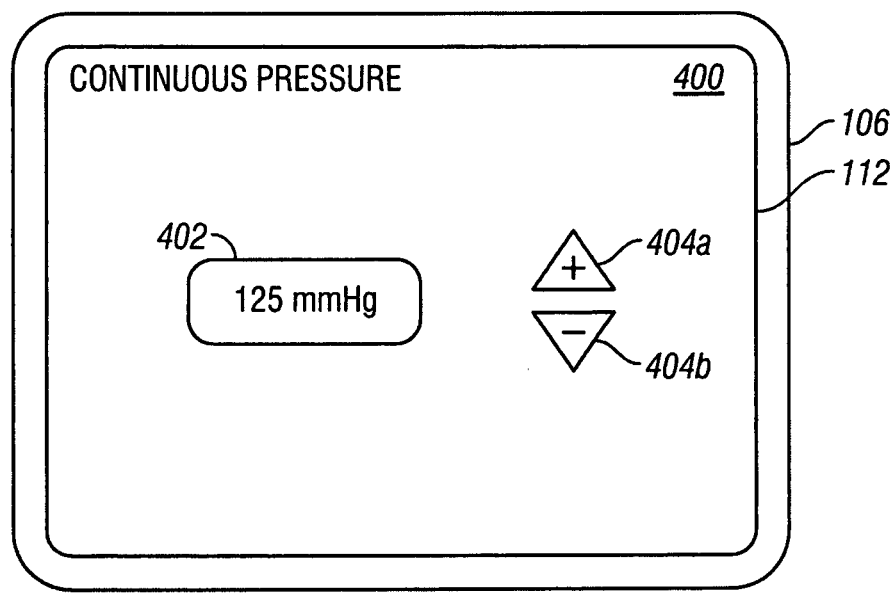
FIG. 4 is an illustration of an exemplary continuous pressure graphical user interface to enable a clinician to select a pressure to be continuously applied to a tissue site of a patient.

Referring to FIG. 4, a Continuous Pressure GUI 400 may be displayed to enable a clinician to change a pressure setting to be applied to a tissue site of a patient. A text display box 402 may display a pressure setting (e.g., 125 mmHg), which may be altered up or down by a clinician pressing a "+" soft-button 404a or "−" soft-button 404b. Although shown as a single, constant pressure, maximum, minimum, and transition pressure settings may alternatively be provided to enable the clinician to apply a varying reduced pressure treatment profile rather than a constant or intermittent one.

Figure 5:
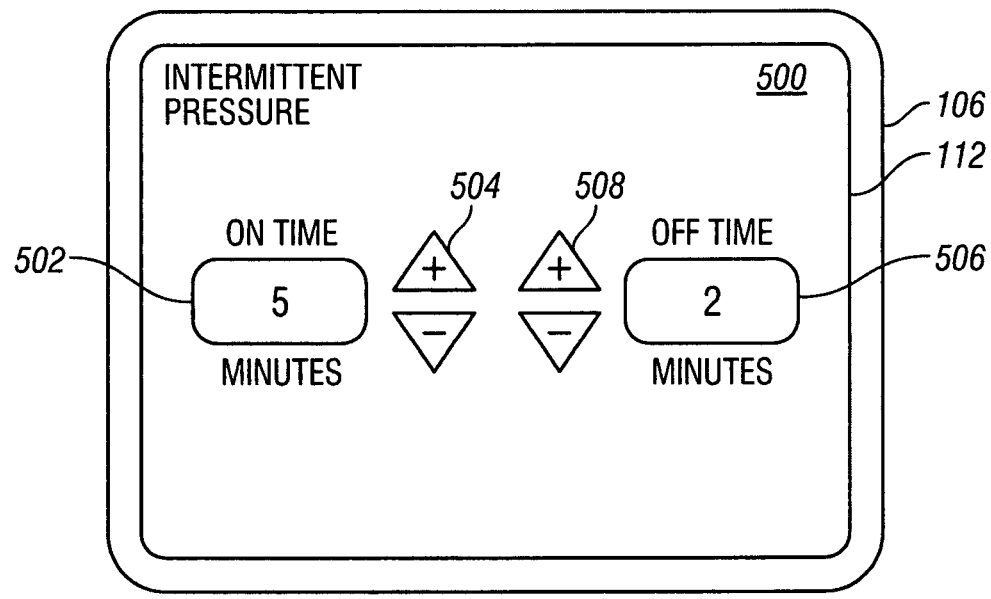
FIG. 5 is an illustration of an exemplary intermittent pressure graphical user interface to enable a clinician to enter and select on and off times to apply an intermittent tissue treatment to a wound site of a patient.

Referring to FIG. 5, an Intermittent Pressure GUI 500 may be displayed to enable a clinician to set intermittent pressure settings to be applied to a tissue site of a patient by the tissue treatment system 106. The Intermittent Pressure GUI 500 may include an "on time" text entry field 502 that defines the amount of time that reduced pressure will be applied to the tissue site (e.g., 5 minutes). The "on time" text entry field 502 may have a value changed by the clinician selecting either a "+" or "−" soft-button 504. An "off time" text entry field 506 may define the amount of time that the reduced pressure will be off between on-times of the reduced pressure. For example, the off time may be set to 2 minutes. Soft-buttons 508 may be used to increase or decrease the off time of the reduced pressure.

Figure 6:
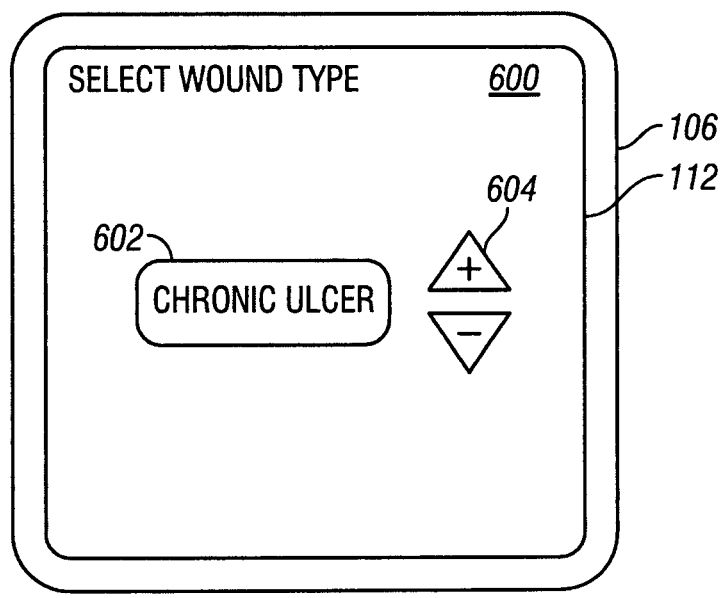
FIG. 6 is an illustration of an exemplary select wound type graphical user interface select a wound type of multiple wound types pre-established to be treated by the tissue treatment system.

Referring to FIG. 6, a Select Wound Type GUI 600 may be displayed to enable a clinician to select a type of wound or tissue type that is to be treated by the tissue treatment system 106. A text field 602 may be utilized to show different wound types that are available for selection. The different wound types are pre-established and have particular pre-established parameters for treating the different wound types. For example, a chronic ulcer may have a different treatment than burn or avulsion wound. Soft-buttons 604 may allow the clinician to display and search through different pre-established wound types. It should be understood that the GUI 600 is exemplary and other interfaces, such as a list with a scroll bar, may be utilized in accordance with the principles of the present invention.

Figure 7:
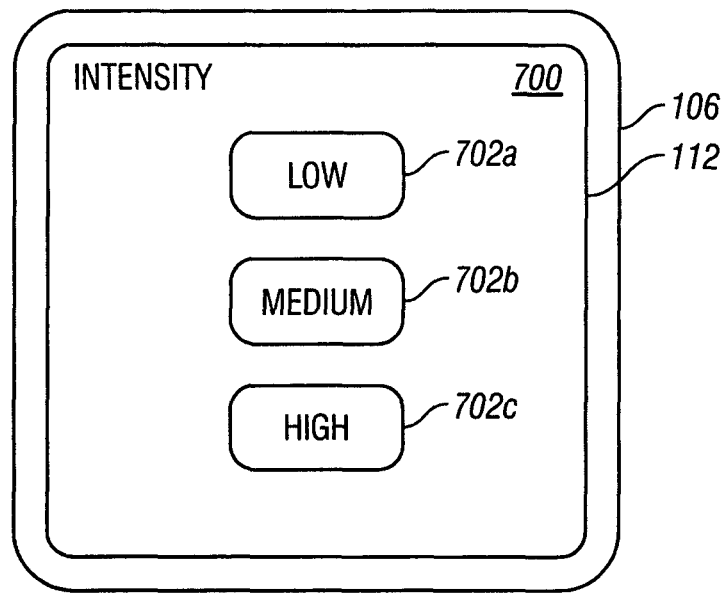
FIG. 7 is an illustration of an exemplary intensity graphical user interface to enable a clinician to select an intensity to apply for a tissue treatment to a tissue site of a patient.

Referring to FIG. 7, an Intensity GUI 700 may be displayed to enable a clinician to select an intensity for the tissue treatment. In one embodiment, the intensity defines how fast the tissue treatment system 106 transitions to a reduced pressure setting. The clinician may select a low, medium, or high intensity by selecting one of soft-buttons 702a, 702b, or 702c, respectively. It should be understood that alternative intensity setting indicia may be selected, including numbers between 1-10, letters A-E, or any other indicia.

Figure 8:
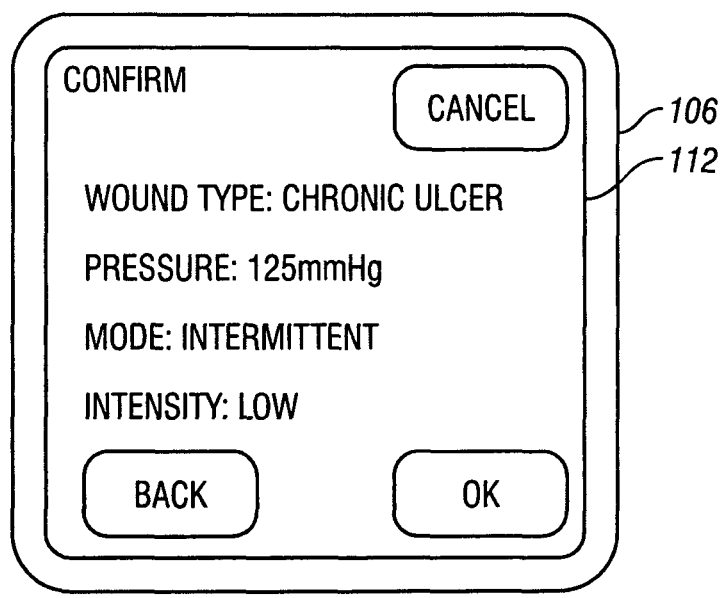
FIG. 8 is an illustration of an exemplary confirmation graphical user interface to confirm a tissue treatment for a tissue site of a patient.

Referring to FIG. 8, a Confirm GUI 800 may be displayed in response to all or some of the settings being selected or set. As shown, the wound type, pressure, mode, and intensity have been set by a clinician preparing to start a tissue treatment. In response to the clinician selecting the "OK" soft-button, the tissue treatment system 106 will commence the tissue treatment.

Figure 9:
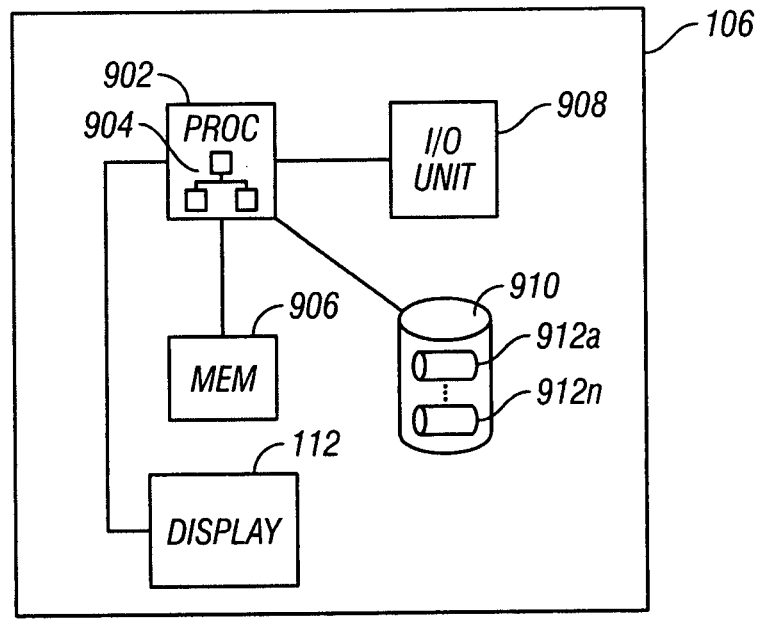
FIG. 9 is a block diagram of an exemplary tissue treatment system to perform tissue treatment to a tissue site of a patient in accordance with the principles of the present invention.

Referring to FIG. 9, the exemplary tissue treatment system 106 may include a processing unit 902 that executes software 904. The processing unit 902 may be configured with one or more processors that are the same or different types. For example, the processing unit 902 may include a general processing unit and a digital signal processing (DSP) unit configured to perform image processing to enable a clinician to edit images of tissue sites, perform color adjustments, tracing, or any other graphical function in accordance with the principles of the present invention.

The processing unit 902 may further be in communication with (i) a memory 906 for storing data and software code, (ii) input/output (I/O) unit 908 for communicating with other devices and systems, such as a digital camera, wirelessly, via a wire, or via a memory input device (not shown), (iii) storage unit 910 that may store one or more data repositories 912a-912n (collectively 912), such as a database having one or more files, and (iv) electronic display 112 that may or may not be touch-sensitive. The software 904 may be configured to interface with each of the other devices (e.g., electronic display 112) to perform tissue site image collection, for example, and color adjust the image of the tissue site by adjusting color for an image of a reference color marker.

Figure 10:
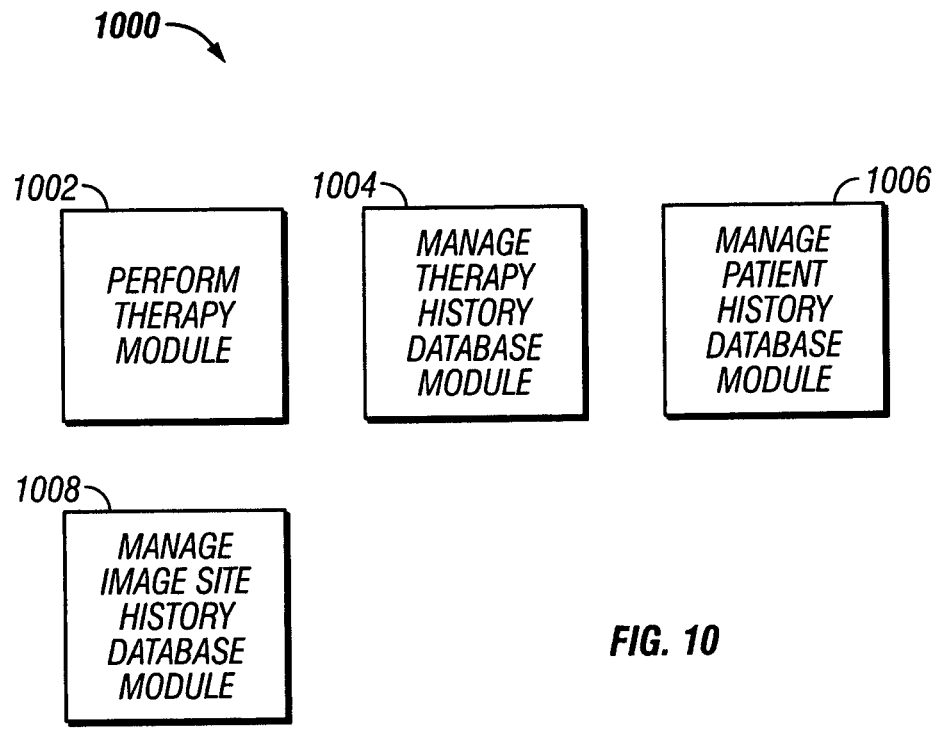
FIG. 10 is a block diagram of software modules for performing functions in accordance with the principles of the present invention.

Referring now to FIG. 10, software modules 1000 of software 904 (FIG. 9) executable by processing unit 902 (FIG. 9) may be utilized to manage databases including history of patients, treatments, and images. The software modules 1000 shown are exemplary and may include additional and/or other software modules to provide the same or similar functionality.

Perform therapy module 1002 is a software module configured to enable a clinician to perform a therapy as established by the clinician. For example, the clinician may set up parameters to perform a continuous reduced pressure treatment with a pressure of 125 mmHg for 30 minutes and the perform therapy module 1002 will execute the reduced pressure therapy treatment on the tissue site of the patient.

Manage therapy history database module 1004 is a software module configured to manage a database that include therapy or treatment history (see FIG. 12). The treatment history may be for one or more patients and show history of reduced therapy applied to tissue of the patient(s). The database may be any type of database, including relational, flat, or other structure as understood in the art. The treatment history database may be part of or related to other databases, such as a patient history database. The module 1004 may be configured to limit access to clinicians and/or doctors.

Manage patient history database module 1006 is a software module configured to manage a database that includes history of patients. In one embodiment, the module 1006 may be configured to limit access to clinicians and/or doctors. Alternatively, a patient on whom the reduced pressure therapy is applied may be enabled to view his or her own treatment history.

Manage image site history database module 1008 is a software module configured to manage tissue site images that are collected of tissue sites from patients over time. Having historical records available on a tissue treatment system may enable a clinician to review the history of the tissue site, patient history, and therapy history and make a decision of continued treatment based on how the tissue site has progressed given therapy that has been performed on the tissue site.

Figure 11:
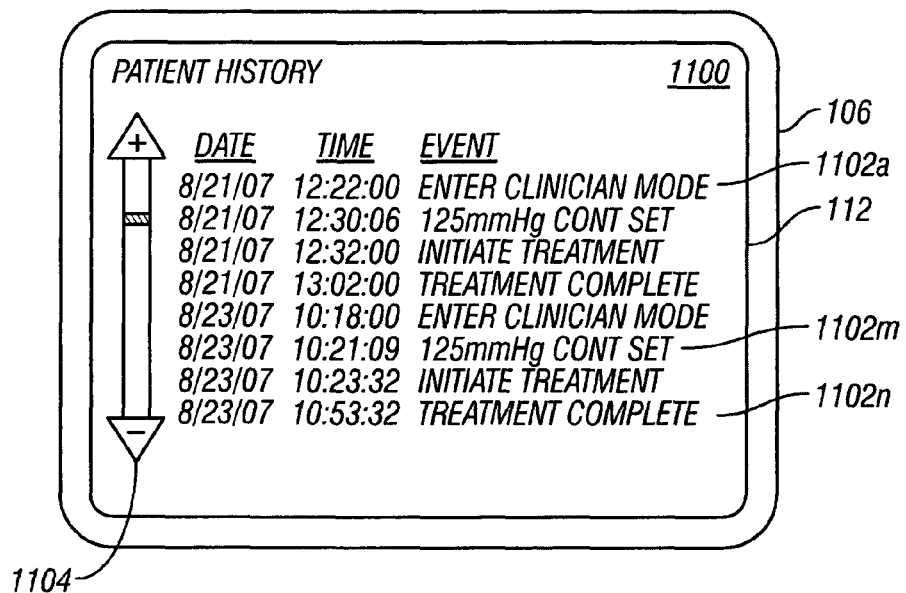
FIG. 11 is a screen shot of an exemplary patient history GUI showing patient history of tissue treatment applied to a tissue site of a patient.
Figure 12:
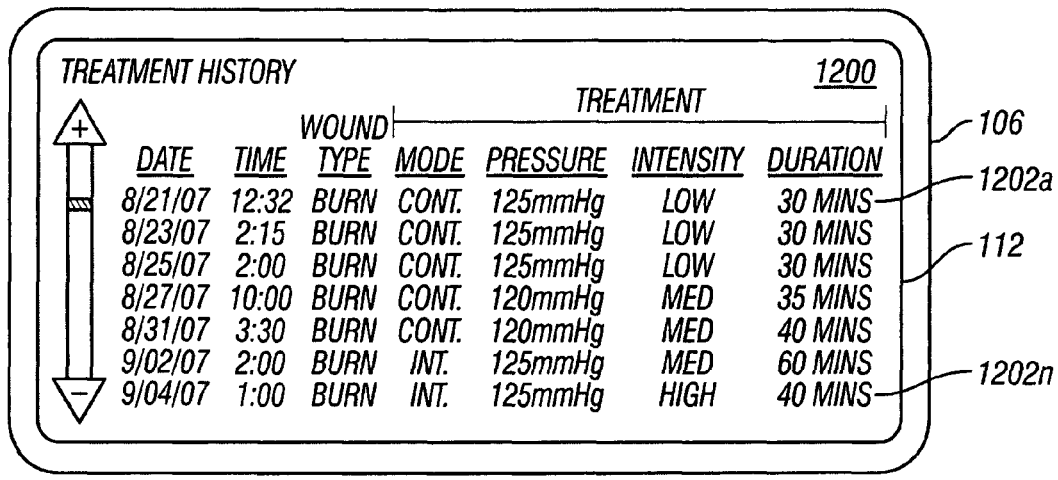
FIG. 12 is a screen shot of an exemplary tissue history GUI showing treatment history of tissue treatment applied to a tissue site of a patient.

Referring to FIG. 11, the tissue treatment system 106 is shown to be displaying a Patient History GUI 1100 with patient history records 1102a-1102n (collectively 1102) on the electronic display 112 of events that have occurred for a patient. A scroll bar 1104 may be provided to enable the clinician to scroll up and down through the list of patient history records 1102. Date, time, and event may be shown. However, other information may be provided to show history of events for a patient. The database may store records for more than one patient and each patient's records may be selectable by the clinician. The clinician may view each event that is entered into the tissue treatment system for a patient. For example, the events may show a "125 mmHg Cont Set" that shows that the clinician sets a continuous pressure of 125 mmHg on Aug. 23, 2007 at time 10:21:09 in record 1102m.

Referring to FIG. 12, the tissue treatment system 106 is shown to be displaying a Treatment History GUI 1200 with treatment history records 1202a-1202n (collectively 1202) on the electronic display 112 of events that have been applied to a tissue site for a patient. The treatment history records 1202 show the date, start time, wound type, mode, pressure, intensity, and duration of treatment each time a treatment is applied to a patient.

Figure 13:
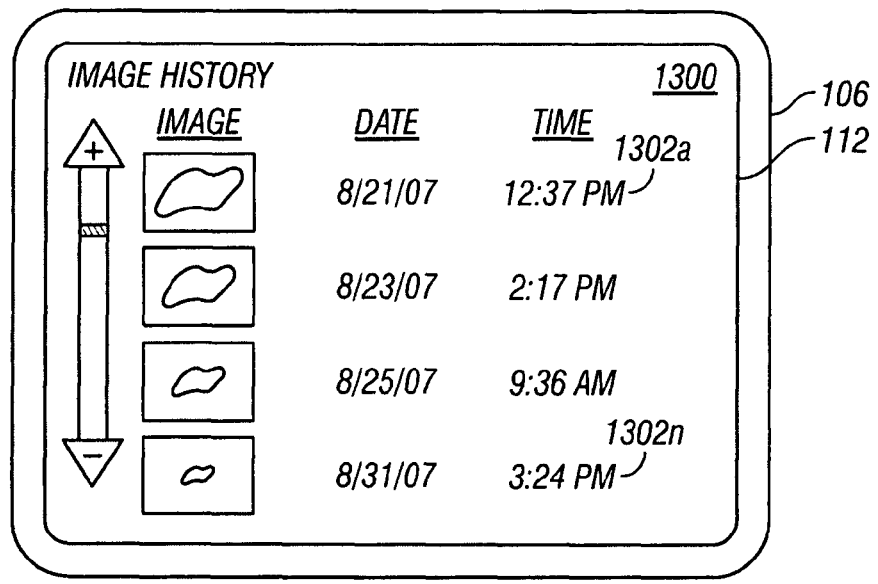
FIG. 13 is a screen shot of an exemplary image history GUI of a tissue site of a patient being treated.

Referring to FIG. 13, the tissue treatment system 106 is shown to be displaying an Image History GUI 1300 with image history records 1302a-1302n (collectively 1302) of tissue sites that are being treated. The image history records 1302 may include a "thumbnail" image, date, and time when each image is captured or communicated to the tissue treatment system 106. A clinician may select a record and expand the image to be full size and optionally zoom into the image to see details of the tissue. If the clinician applies traces, outlines, notes, areas, volumes, or other information to an image, the image may be maintained as a raw image and the information may be maintained separate or a second image with the information may be maintained in the database. The database may be a relational database or any other type of database and be related to the patient history database and treatment history database.

Figure 14:
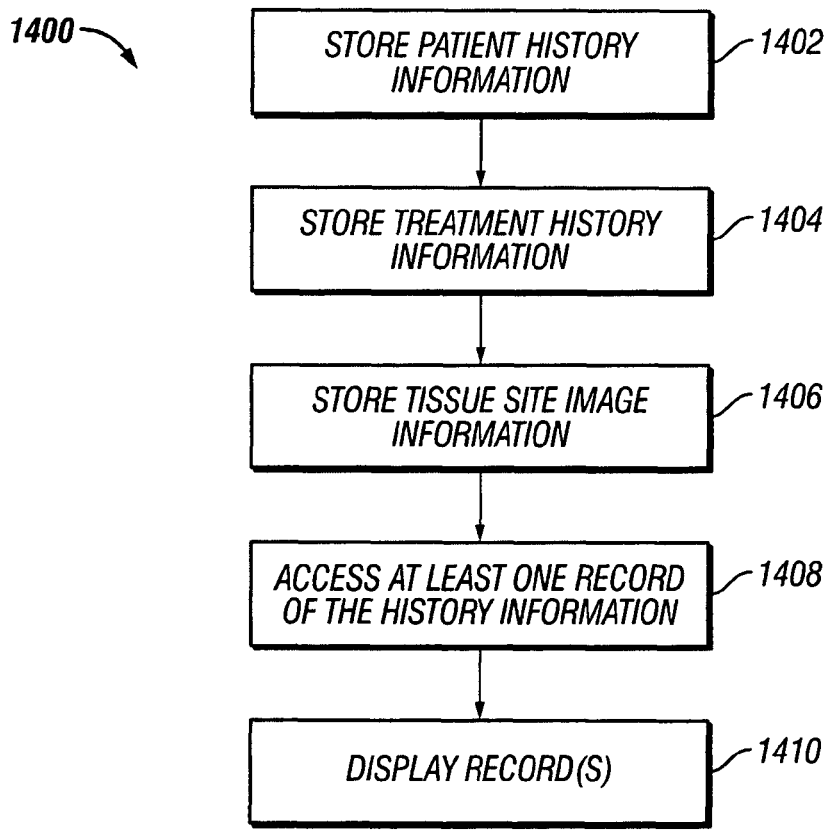
FIG. 14 is a flow chart of an exemplary process for storing and accessing historical patient, treatment, and tissue site image information to be used to assist a clinician for determining tissue treatments.

Referring to FIG. 14, an exemplary process 1400 for storing patient, tissue treatment, and tissue site image information is provided. The process 1400 starts at step 1402, where patient history information may be stored. At step 1404, treatment history information may be stored. At step 1406, tissue site image information may be stored. At step 1408, at least one record of the history information may be accessed. The record(s) may be displayed to enable a clinician to make tissue treatment decisions based on historical treatment provided to the patient and results of the tissue treatment to the tissue site being treated.

Although the principles of the present invention have been described in terms of the foregoing embodiments, this description has been provided by way of explanation only, and is not intended to be construed as a limitation of the invention. Those skilled in the art will recognize modifications of the present invention that might accommodate specific patient and wound healing environments. Such modifications as to size, and even configuration, where such modifications are merely coincidental to the type of wound or to the type of therapy being applied, do not necessarily depart from the spirit and scope of the invention.

We claim:

1. A reduced pressure tissue treatment system, comprising:
a processing unit executing software;
an electronic display in communication with said processing unit; and
a storage unit in communication with said processing unit, the software configured to cause said processing unit to:
manage a patient history database, treatment history database, and image history database to store patient history, treatment history, and image history, respectively, of one or more patients being treated by the reduced pressure tissue treatment system;
enable a clinician to access and display information stored in any of the databases;
enable a clinician to enter tissue treatment parameters;
apply a reduced pressure to a tissue site of a patient using a vacuum pump of the reduced pressure tissue treatment system based on the tissue treatment parameters, the reduced pressure applied to the tissue site defining a treatment;
generate tissue treatment information representative of the treatment performed on the patient by the reduced pressure tissue treatment system;
store the tissue treatment information in the treatment history database; and
in response to the clinician entering a query to access the tissue treatment information from the treatment history database, display the tissue treatment information on the reduced pressure tissue treatment system.

2. The reduced pressure tissue treatment system according to claim 1, further comprising:
an image capture device configured to capture an image of a tissue site; and
an input/output unit in communication with said processing unit, and configured to receive the image of the tissue site captured by said image capture device.

3. The reduced pressure tissue treatment system according to claim 1, further comprising:
a touch-screen electronic display in communication with said processing unit, and the software configured to enable a clinician access any of the patient, treatment, and image history via the touch-screen electronic display.

4. The reduced pressure tissue treatment system according to claim 1, wherein the patient history includes a record identifying date, time, and event in performing a tissue treatment on a patient.

5. The reduced pressure tissue treatment system according to claim 1, wherein the treatment history database includes a record identifying date, time, mode, pressure, and duration of treatment.

6. The reduced pressure tissue treatment system according to claim 1, wherein the image history database includes a record including an image, date, and time of image captured.

7. The reduced pressure tissue treatment system according to claim 6, wherein said processing unit is further configured to display thumbnail images of a tissue site over time and enable a clinician to selectively expand an image.

8. The reduced pressure tissue treatment system according to claim 7, wherein said processing unit is further configured to display graphics on the expanded image to show an outline of the tissue site.

9. The reduced pressure tissue treatment system according to claim 1, wherein the software is further configured to enable the clinician to select one of a plurality of wound types as a tissue treatment parameter.

10. A method for managing tissue treatment information on a reduced pressure tissue treatment system, comprising:
storing patient history information in a storage unit in communication with a processing unit for executing software, the storage unit and processing unit operating in the reduced pressure tissue treatment system;
storing treatment history information in the storage unit;
storing image history information of a tissue site of a patient in the storage unit, the image history information be indicative of results of tissue treatment to the tissue site;
accessing at least one record of patient, treatment, and image history information;
displaying the at least one record to enable a clinician to make tissue treatment decisions based on historical treatment provided to the patient and results of the tissue treatment to the tissue site being treated;
enabling the clinician to enter tissue treatment parameters;
applying a reduced pressure to a tissue site of a patient using a vacuum pump of the reduced pressure tissue treatment system based on the tissue treatment parameters, the reduced pressure applied to the tissue site defining a treatment;
generating tissue treatment information representative of the treatment performed on the patient by the reduced pressure tissue treatment system;
storing the tissue treatment information in the treatment history database; and
in response to the clinician entering a query to access the tissue treatment information from the treatment history database, displaying the tissue treatment information on the reduced pressure tissue treatment system.

11. The method according to claim 10, further comprising:
capturing an image of a tissue site; and
receiving the captured image of the tissue site.

12. The method according to claim 10, further comprising:
enabling a clinician to access any of the patient, treatment, and image history via a touch-screen electronic display.

13. The method according to claim 10, wherein storing patient history includes storing a record identifying date, time, and event in performing a tissue treatment on a patient.

14. The method according to claim 10, wherein storing treatment history includes storing a record identifying date, time, mode, pressure, and duration of treatment.

15. The method according to claim 10, wherein storing image history includes storing a record including an image, date, and time of image captured.

16. The method according to claim 15, further comprising:
displaying thumbnail images of a tissue site over time; and
enabling a clinician to selectively expand an image.

17. The method according to claim 16, further comprising displaying graphics on the expanded image to show an outline of the tissue site.

18. The method according to claim 10, further comprising receiving a selection of one of a plurality of wound types as a tissue treatment parameter.

19. The reduced pressure tissue treatment system to claim 1, wherein the treatment parameters used in performing the tissue treatment are stored in the treatment history database.

20. The reduced pressure tissue treatment system to claim 19, wherein the treatment parameters are associated with the respective patient on which the tissue treatment has been performed.

* * * * *